United States Patent [19]

Kienzle

[11] 4,204,073

[45] May 20, 1980

[54] PROCESS FOR PRODUCING CAROTENOIDS

[75] Inventor: Frank Kienzle, Flüh, Switzerland

[73] Assignee: Hoffmann-La Roche Inc., Nutley, N.J.

[21] Appl. No.: 27,624

[22] Filed: Apr. 6, 1979

Related U.S. Application Data

[62] Division of Ser. No. 815,470, Jul. 14, 1977, abandoned.

[30] Foreign Application Priority Data

Aug. 2, 1976 [AT] Austria ................................. 5705/76

[51] Int. Cl.² ...................... C07C 69/52; C07C 67/02

[52] U.S. Cl. .................................. 560/231; 560/129; 560/187; 560/188; 560/219; 560/220; 560/228; 260/408; 260/410; 568/838; 568/379; 568/363; 568/361; 568/367; 568/11; 568/343; 568/350; 568/347

[58] Field of Search .................. 260/408, 410, 586 R; 560/129, 187, 188, 219, 220, 288, 231; 568/838

[56] References Cited

U.S. PATENT DOCUMENTS

| | | | |
|---|---|---|---|
| 3,781,314 | 12/1973 | Bollag | 260/410.9 R |
| 3,975,445 | 8/1976 | Kienzle | 260/590 C |
| 4,025,564 | 5/1977 | Rosenberger | 260/606.5 F |

*Primary Examiner*—John F. Niebling
*Attorney, Agent, or Firm*—Jon S. Saxe; Bernard S. Leon; William H. Epstein

[57] ABSTRACT

A process for producing trimethyl oxo or hydroxy substituted cycopentenone food coloring agents including intermediates in this process.

4 Claims, No Drawings

PROCESS FOR PRODUCING CAROTENOIDS

This is a division, of application Ser. No. 815,470 filed July 14, 1977 now abandoned.

SUMMARY OF INVENTION

The present invention relates to polyene compounds. More particularly, the invention is concerned with novel carotenoid polyene compounds and a process for the manufacture of these compounds and of derivatives thereof.

The novel polyene compounds provided by the present invention have the following formula

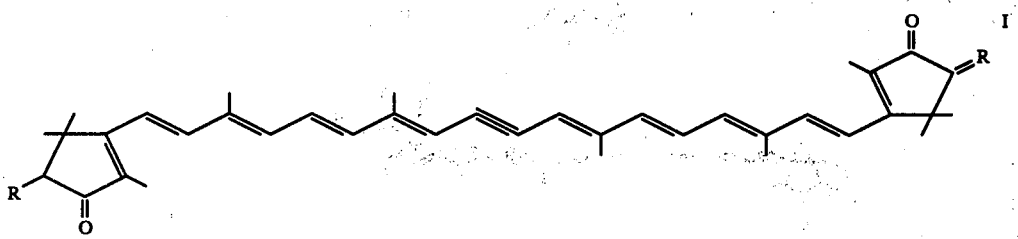

wherein R is oxo or acyloxy and the broken lines denote optional carbon-carbon bonds.

The polyene compounds of the formula which are embraced by formula I hereinbefore, are deep-red pigments which are suitable for the coloring of foodstuffs, pharmaceuticals and cosmetic preparations. They are also key substances for the manufacture of violerythrin and actinioerythrol.

Violerythrin [2,2'-dinor-astacene] has a deep blue color which is suprising for a carotenoid. Violerythrin can be converted by reduction into the red actinioerythrol [2,2'-dinor-astaxanthin]. Moreover, actinioerythrol can be oxidized in solution to violerythrin by simply blowing air through the solution.

DETAILED DESCRIPTION OF INVENTION

Violerythrin has hitherto been obtainable in large amounts only by oxidation of 2,2'-dinor-canthaxanthin. Violerythrin is now especially readily accessible from the novel polyene compounds of formula I hereinbefore as shown in the following Reaction Scheme:

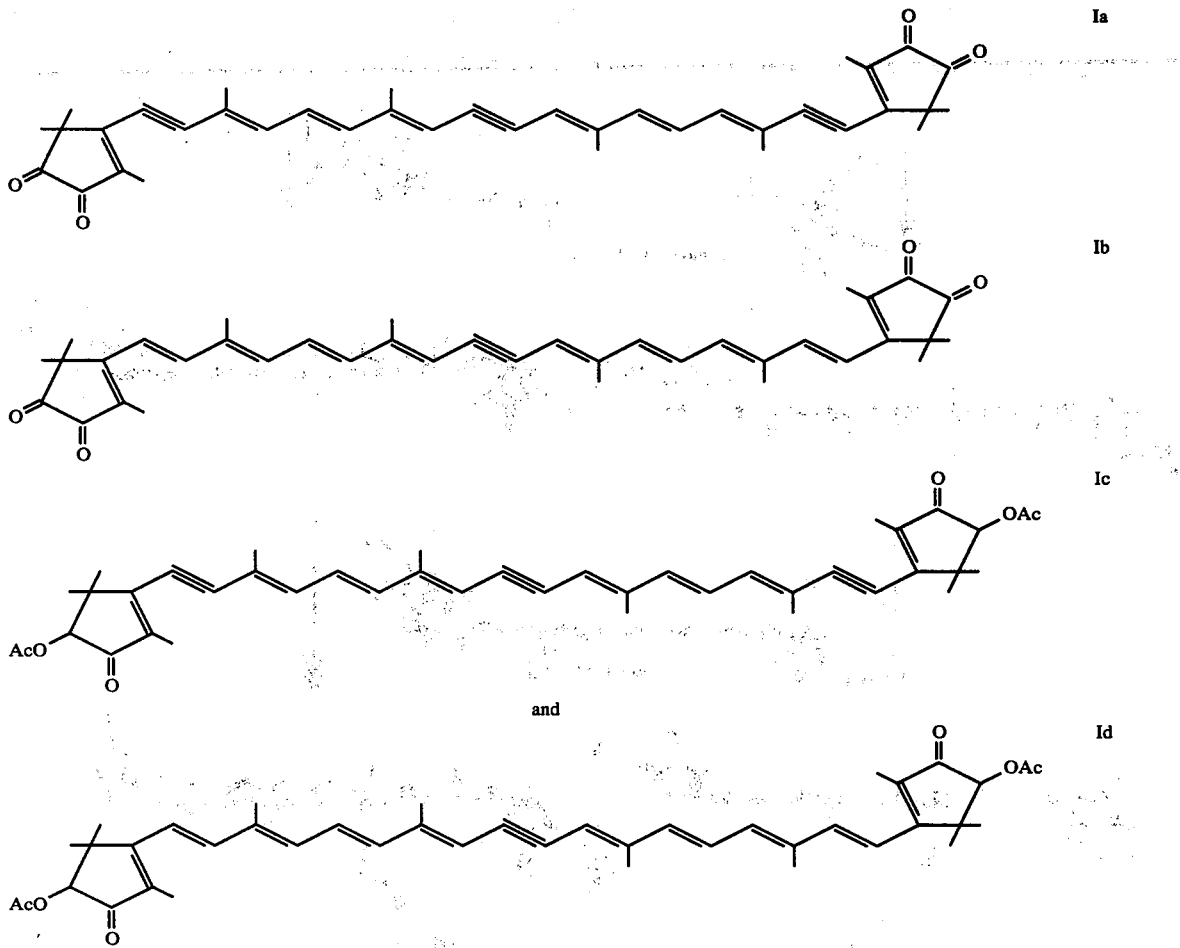

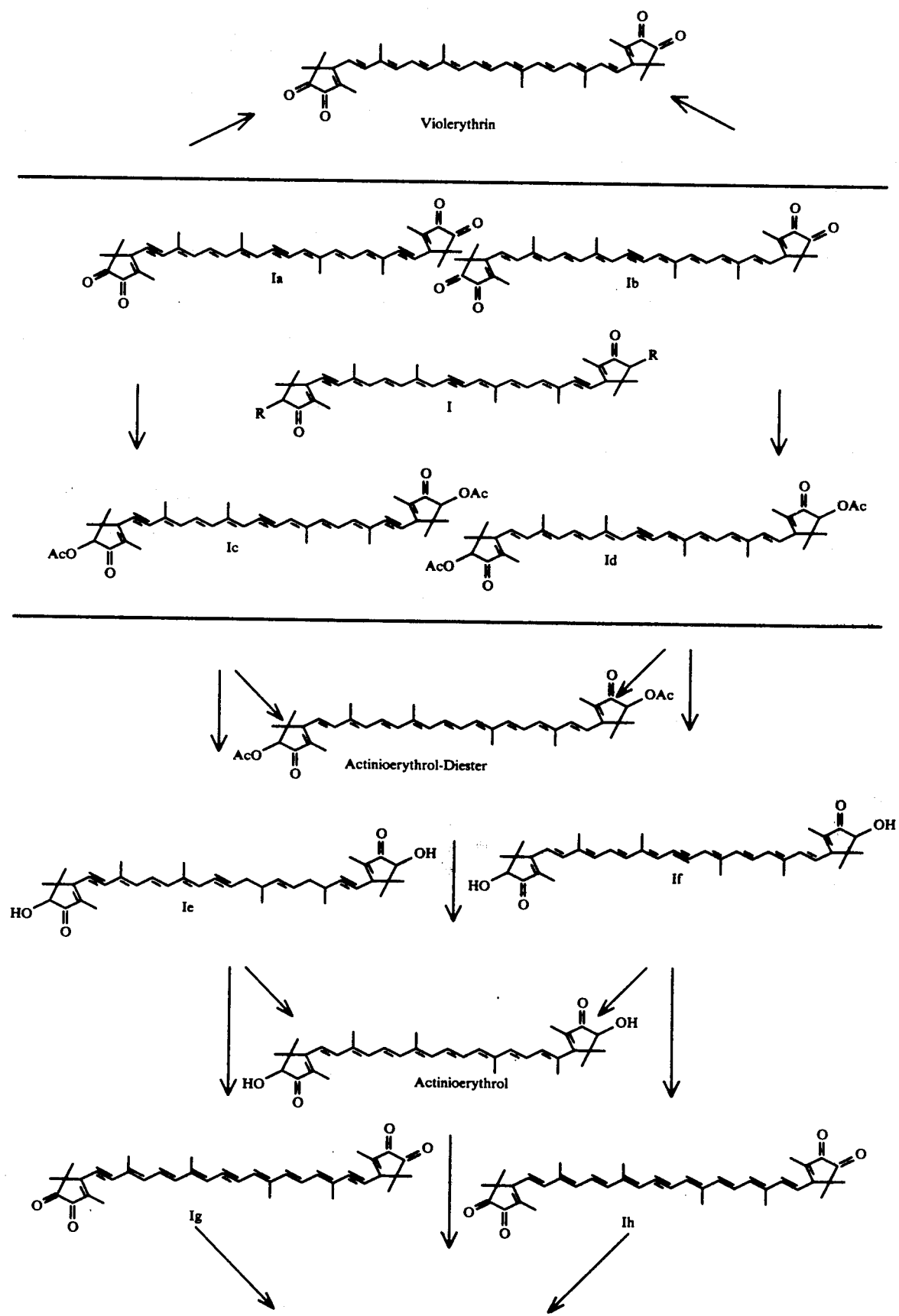

-continued

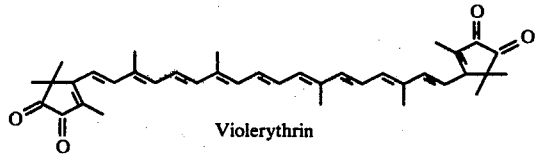
Violerythrin

The process privided by the present invention for the manufacture of the polyene compounds of formula I comprises reacting a compound of the formula

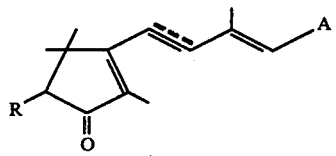  II with a compound of the general formula

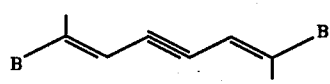  III wherein R is oxo or acyloxy; one of A and B is formyl and the other is triarylphosphoniummethyl having the formula —$CH_2$-P[X]$_3$ $\oplus$Y$\ominus$; X is aryl; and Y is an anion of an organic or inorganic acid; and the broken line denotes an optional carbon-carbon bond,
to give a polyene compound of the general formula

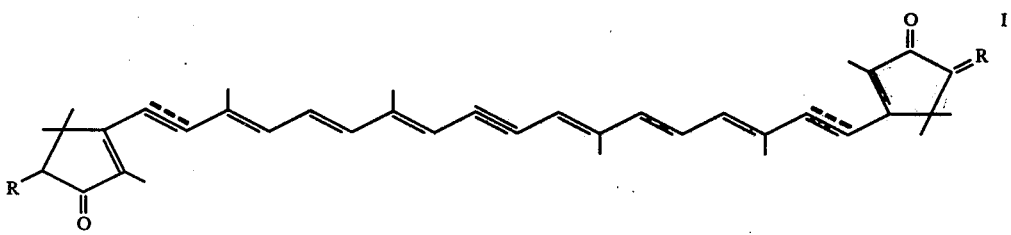  I wherein R and the broken lines are as above, and, if desired, converting the compound of formula I in which R is oxo by partial hydrogenation into violerythrin, or converting a compound of formula I in which R is acyloxy in optional sequence by partial hydrogenation and saponification into actinioerythrol or by partial hydrogenation, saponification and oxidation or saponification, oxidation and partial hydrogenation into violerythrin.

Of the aforementioned embodiments for the manufacture of the polyene compounds of formula I there have been found to be especially convenient the procedures denotes as (a), (b), (c) and (d) hereinafter, namely the reaction of (a) a phosphonium salt of the general formula

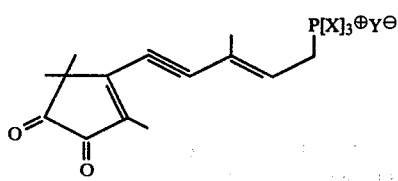  IIA wherein X and Y are as above;
or (b) a phosphonium salt of the general formula

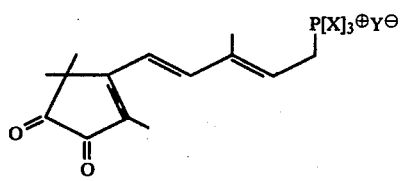  IIB wherein X and Y are as above;
or (c) a phosphonium salt of the general formula

  IIC wherein R' is an acyloxy group and X and Y are as above,
or (d) a phosphonium salt of the general formula

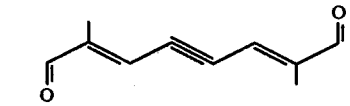  IID wherein R', X and Y are as above;
with the dialdehyde of the formula

IIIA

The starting materials are reacted with one another by means of a Wittig reaction in the presence of an acid-binding agent, for example an alkali metal hydroxide such as potassium hydroxide, an alkali metal alcoholate such as sodium methylate or an alkylene oxide which may be alkyl-substituted, especially in the presence of ethylene oxide or 1,2-butylene oxide, if desired in a solvent, for example an alkanol such as isopropanol, a chlorinated hydrocarbon such as methylene chloride or dimethylformamide, at a temperature between room temperature and the boiling point of the reaction mixture.

An acyloxy group denoted by R or R' is derived from a lower or higher alkanecarboxylic acid or alkenecarboxylic acid. The lower members contain from 1 to 6 carbon atoms and the higher members contain from 7 to 20 carbon atoms. Both members can be substituted by halogen, alkoxy or aryloxy. Examples of the lower members are the acetoxy, propionyloxy, butyryloxy, valeryloxy, caprylyloxy, monochloroacetoxy, dichloroacetoxy, ethoxyacetoxy and phenoxyacetoxy groups. Examples of the higher members are the palmitoyloxy, stearoyloxy and oleoyloxy groups. The term aryl denotes aryl groups such as phenyl and napthyl.

The acyloxy groups substituted by halogen, alkoxy or aryloxy can be saponified to the hydroxy group without this being converted partially into the oxo group during the saponification.

When it is desired to convert a polyene compound of formula Ic or Id by the aforementioned procedures into actinioerythrol, then such polyene compounds must be substituted by one of the previously mentioned acyloxy groups which are readily cleavable by hydrolysis. When a normal ester of formula Ic or Id is used (e.g. the acetic acid or the palmitic acid ester), then the hydroxy group initially liberated during the saponification is converted immediately into the oxo group under the conditions required for the cleavage of the acyl groups, and violerythrin is obtained as the end product.

Of the acyloxy groups which are cleavable under mild conditions there occupy a preferred position the acyloxy groups substituted by chloro or phenoxy, which can be saponified to the hydroxy group by means of weak alkalis at a temperature between about −30° C. and +50° C. The monochloroacetoxy and dichloroacetoxy groups can even be hydrolyzed by mere heating in water or in an aqueous alkanol. The (trichloro or trifluoro) acetoxy group is less suitable as the protecting group because of its lability.

The starting materials of the general formulae

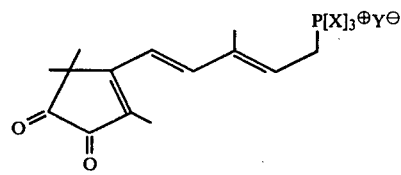

and

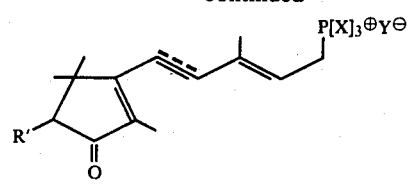

wherein R', X, Y and the broken line have the significance given earlier,
used in embodiments (a), (b), (c) and (d) of the process are novel and also form part of the present invention. They can be prepared from a common key compound of the formula

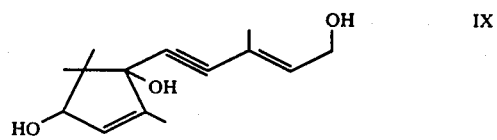

which is likewise novel and also forms part of the present invention.

The preparation of the starting materials of formula IIAB starting from the triol of formula IX is illustrated in the following Reaction Scheme in which X and Y are as above.

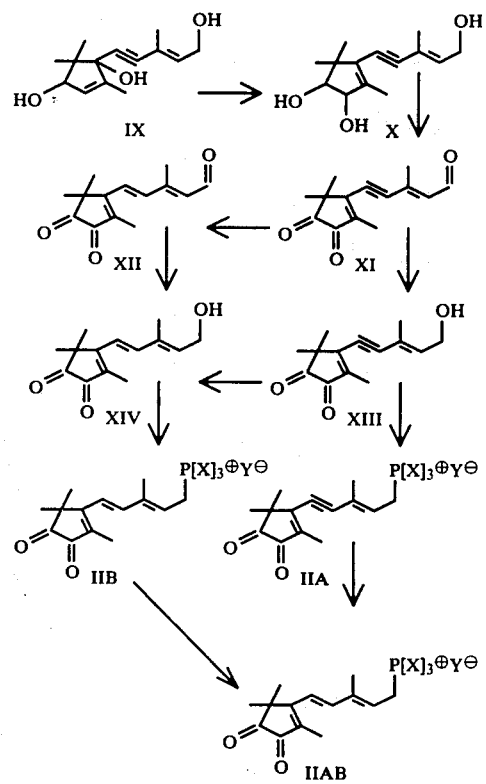

The preparation of the starting materials of formula IICD starting from the triol of formula IX is illustrated in the following Reaction Scheme in which R', X and Y are as above.

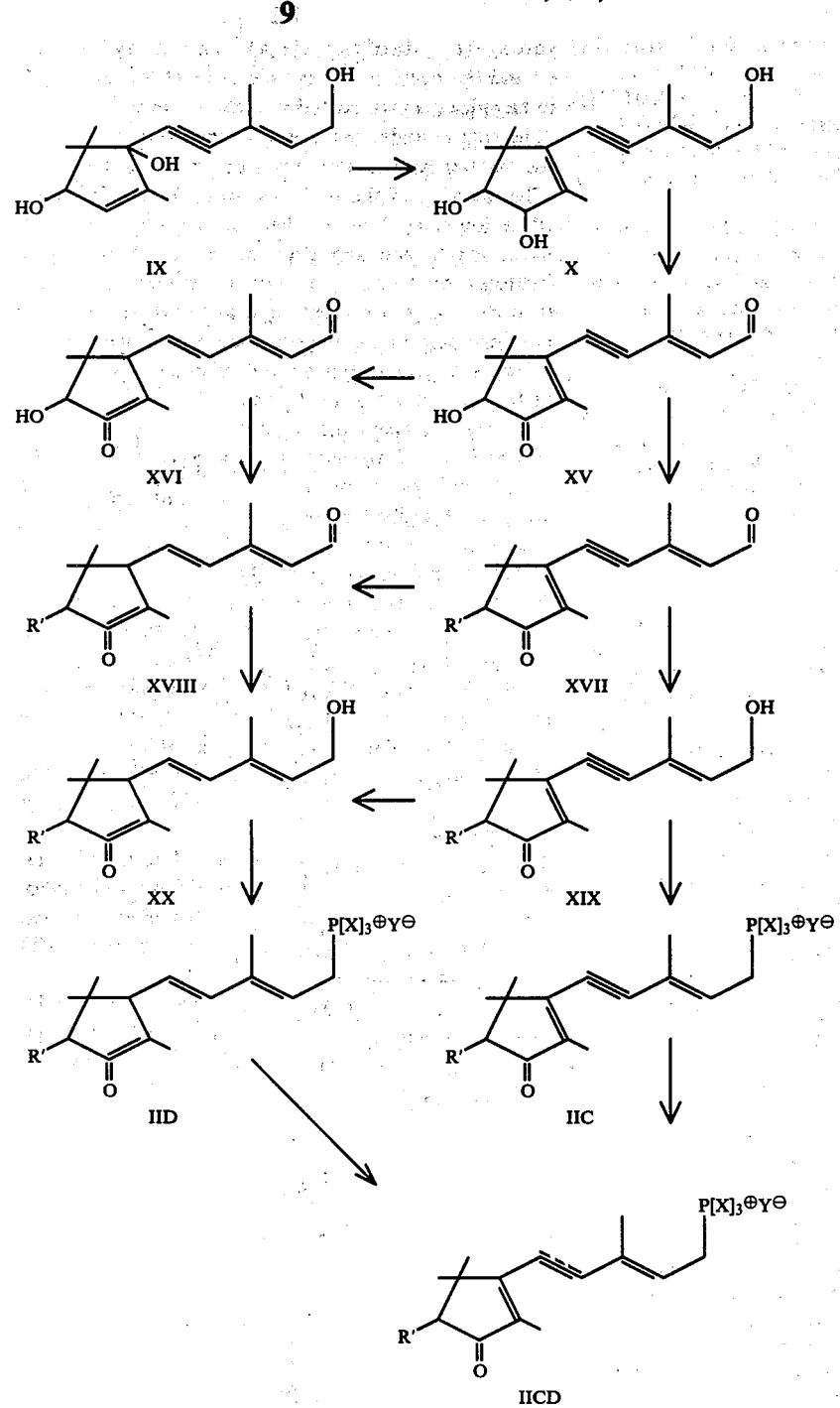

The preparation of the starting materials of formula IIAB is carried out, in general, as follows:

The triol of formula IX, 5-[1,4-dihydroxy-2,5,5-trimethyl-cyclopent-2-en-1-yl]-3-methyl-pent-2-en-4-yn-1-ol is first subjected to an allyl rearrangement to give the triol of formula X, 5-[3,4-dihydroxy-2,5,5-trimethyl-cyclopent-1-en-1-yl]-3-methyl-pent-2-en-4-yn-1-ol. The allyl rearrangement is conveniently carried out in an aqueous mineral acid such as sulfuric acid, if desired in the presence of a solvent such as acetone or tetrahydrofuran, or in an organic acid such as formic or acetic acid. If an organic acid is used, then the ester which intermediately results must be saponified (e.g. with an aqueous sodium carbonate solution).

The resulting triol of formula X is subsequently oxidized to the aldehyde of formula XI, 5-[3,4-dioxo-2,5,5-trimethyl-cyclopent-1-en-1-yl]-3-methyl-pent-2-en-4-yn-1-al. The oxidation can be carried out, for example, using nickel peroxide or manganese dioxide. The oxidation is conveniently carried out in a solvent such as diethyl ether, ethyl acetate, dioxan or benzene, and at a temperature between −30° C. and the boiling point of the oxidation mixture.

The resulting acetylenic ketoaldehyde of formula XI is then either partially hydrogenated to the olefinic ketoaldehyde of formula XII, 5-[3,4-dioxo-2,5,5-trimethyl-cyclopent-1-en-1-yl]-3-methyl-penta-2,4-dien-1-al, which is subsequently reduced to the olefinic ketoalcohol of formula XIV, 5-(3,4-dioxo-2,5,5-trimethyl-cyclopent-1-en-1-yl]-3-methyl-penta-2,4-dien-1-ol, or reduced to the acetylenic ketoalcohol of formula XIII, 5-[3,4-dioxo-2,5,5-trimethyl-cyclopent-1-en-1-yl]-3-methyl-pent-2-en-4-yn-1-ol, which is subsequently partially hydrogenated to the olefinic ketoalcohol of formula XIV.

The partial hydrogenation of the ethynylene to the vinylene group is carried out in a manner known per se using a partially deactivated palladium catalyst (Lindlar catalyst) in a solvent such as benzene, toluene, ethyl acetate or an alkanol such as methanol, conveniently at normal pressure and room temperature.

The conversion of the ketoaldehydes of formulae XI and XII into the ketoalcohols of formulae XIII and XIV is carried out using a reducing agent, for example sodium borohydride in ethanol, dimethylformamide, tetrahydrofuran or diethyleneglycol dimethyl ether, or sodium dihydro-bis(2-methoxyethoxy)aluminate or diisobutylaluminium hydride in tetrahydrofuran or dimethyl ether, at a temperature below 0° C., particularly at −30° C.

The resulting ketoalcohols of formulae XIII and XIV are subsequently converted by treatment with a halogenating agent, for example phosphorus tribromide, phosphorus oxychloride, thionyl chloride or phosgene in an ether or in dimethylformamide or N-bromosuccinimide in the presence of dimethylsulfide, into the corresponding halides, which are converted by reaction with a triarylphosphine (e.g. triphenylphosphine) into the phosphonium salts of formulae IIA and IIB which can be generically formulated under formula IIAB.

The preparation of the starting materials of formula IICD is carried out, in general, as follows:

The triol of formula X obtained as previously described from the triol of formula IX by allyl rearrangement is oxidized to the aldehyde of formula XV, 5-[3-oxo-4-hydroxy-2,5,5-trimethyl-cyclopent-1-en-1-yl]-3-methyl-pent-2-en-4-yn-1-al. The oxidation is carried out in the same manner as previously described for the oxidation of the triol of formula X to the aldehyde of formula XI. As the oxidation agent there is, however, conveniently used 2,3-dichloro-5,6-dicyano-benzoquinone since this guarantees the desired selectivity.

The resulting acetylenic hydroxyaldehyde of formula XV is either partially hydrogenated to the olefinic hydroxyaldehyde of formula XVI, 5-[3-oxo-4-hydroxy-2,5,5-trimethyl-cyclopent-1-en-1-yl]-3-methyl-penta-2,4-dien-1-al, which is subsequently esterified to an olefinic ester of formula XVIII, a 5-[3-oxo-4-acyloxy-2,5,5-trimethylcyclopent-1-en-1-yl]-3-methyl-penta-2,4-dien-1-al, or esterified to an acetylenic ester of formula XVII, a 5-[3-oxo-4-acyloxy-2,5,5-trimethyl-cyclopent-1-en-1-yl]-3-methyl-pent-2-en-4-yn-1-al which is subsequently partially hydrogenated if desired to the olefinic ester of formula XVIII.

The sequence in which the partial hydrogenation of the acetylenic compound and the masking of the hydroxy group is carried out is determined by the choice of the esterification agent. When there is used a halogenated carboxylic acid, the halogen atom of which could poison the catalyst, such as, for example, monochloroacetic acid or dichloroacetic acid, then it is recommended to initially partially hydrogenate the acetylenic hydroxyaldehyde of formula XV and subsequently to esterify the resulting olefinic hydroxyaldehyde of formula XVI. On the other hand, when there is used a halogen-free esterification agent, then the acetylenic hydroxyaldehyde of formula XV can initially be esterified and the resulting acetylenic ester of formula XVII can be subsequently partially hydrogenated.

The partial hydrogenation is carried out in an analogous manner to that previously described in detail.

The masking of the hydroxy group by esterification with a lower or higher alkanecarboxylic acid or alkenecarboxylic acid anhydride or halide, which may be substituted by halogen, alkoxy or aryloxy, is carried out, if desired in a solvent such as tetrahydrofuran or methylene chloride, in the presence of an organic nitrogen base such as pyridine or triethylamine at a temperature between about −30° C. and +50° C.

The resulting masked ketoaldehydes of formulae XVII and XVIII are subsequently converted into the ester alcohols of formulae XIX and XX in the same manner as described earlier for the conversion of the ketoaldehydes of formulae XI and XII into the ketoalcohols of formulae XIII and XIV.

The resulting ester alcohols of formulae XIX and XX are subsequently converted, in the same manner as previously described in connection with the alcohols of formulae XIII and XIV, via the halides into the phosphonium salts of formulae IIC and IID which can be generically formulated under formula IICD.

The dialdehyde starting material of formula IIIA, 2,7-dimethyl-octa-2,6-dien-4-yne-1,8-dial, is a known compound.

Likewise known is the analogous 2,7-dimethyl-octa-2,4,6-trien-1,8-dial which, by reaction with a phosphonium salt of formula IIB directly yields violerythrin and by reaction with a phosphonium salt of formula IID directly yields actinioerythrol.

The aforementioned key compound of formula IX can be obtained, for example, from 2,5,5-trimethyl-cyclopent-2-ene-1,4-dione of formula IV as shown in the following Reaction Scheme:

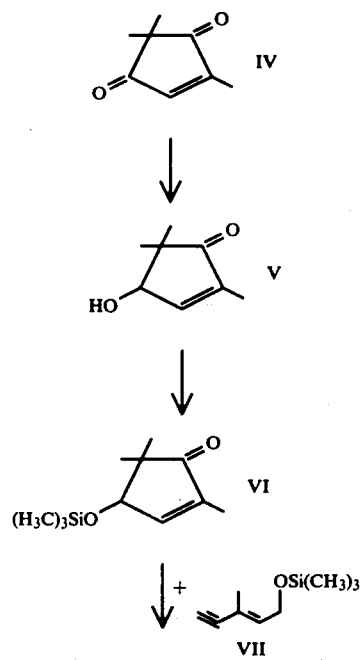

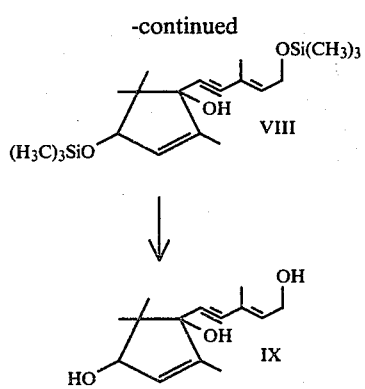

The individual steps of this Reaction Scheme are carried out, for example, as follows:

The known 2,5,5-trimethyl-cyclopent-2-en-1,4-dione of formula IV is dissolved in an organic solvent (e.g. an alkanol) and reduced at a temperature below 0° C. with sodium borohydride. The desired 4-hydroxy-2,5,5-trimethyl-cyclopent-2-en-1-one of formula V is isolated by rectification from the isomeric mixture which occurs during the working-up.

The 4-hydroxy-2,5,5-trimethyl-cyclopent-2-en-1-one of formula V is an important compound in the preparation of the aforementioned key compound of formula IX. The 4-hydroxy-2,5,5-trimethyl-cyclopent-2-en-1-one of formula V is novel and also forms part of the present invention.

The hydroxy group of the hydroxyketone of formula V is subsequently masked by treatment with trimethylchlorosilane in the presence of an organic nitrogen (e.g. triethylamine) in diethyl ether in the cold at about 0° C.

The resulting 2,5,5-trimethyl-4-[(trimethylsilyl)oxy]-cyclopent-2-en-1-one of formula VI is then condensed in a solvent (e.g. tetrahydrofuran) by means of a Grignard reaction with trimethyl-[(trans-3-methyl-pent-2-en-4-yn-1-yl)oxy]-silane of formula VII to give 5-[2,5,5-trimethyl-1-hydroxy-4-[(trimethylsilyl)oxy]-cyclopent-2-en-1-yl]-3-methyl-1-[(trimethylsilyl)oxy]-pent-2-en-4-yne of formula VIII which, without isolation, is saponified by shaking with a dilute aqueous alkali hydroxide solution to give 5-[1,4-dihydroxy-2,5,5-trimethyl-cyclopent-2-en-1-yl]-trans-3-methyl-pent-2-en-4-yn-1-ol of formula IX.

The aforementioned trimethyl-[(trans-3-methyl-pent-2-en-4-yn-4-yl)-oxy]-silane of formula VII can be readily obtained by the action of trimethylchlorosilane at room temperature on trans-3-methyl-pent-2-en-4-yne in an ether such asdimethyl ether in the presence of an organic nitrogen base such as triethylamine.

The following Examples illustrate the present invention:

The Lindlar catalyst utilized is a mixture of palladium/calcium carbonate and lead oxide.

The ether utilized is diethyl ether.

EXAMPLE 1

After the addition of 150 ml of butylene oxide, 8.1 g of 5-[3,4-dioxo-2,5,5-trimethyl-cyclopent-1-en-1-yl]-3-methyl-penta-2,4-diene-1-triphenylphosphonium bromide and 820 mg of 2,7-dimethyl-octa-2,6-dien-4-yn-1,8-dial are stirred at room temperature for 5 hours. The mixture is then introduced into water and extracted with methylene chloride. The extract is evaporated under reduced pressure. The residual 15,15'-didehydroviolerythrin is purified by adsorption on silica gel. U.V. maximum: 520 nm (in chloroform).

EXAMPLE 2

5.6 of 15,15'-didehydroviolerythrin are dissolved in 1000 ml of toluene. After the addition of 2 g of partially deactivated palladium catalyst (Lindlar catalyst), the solution is shaken in a hydrogen atmosphere at room temperature and normal pressure until the calculated amount of hydrogen has been taken up. The catalyst is then separated. The filtrate is evaporated under reduced pressure. The residual violerythrin melts at 236°–238° C. after recrystallization from methylene chloride/hexane. U.V. maximum: 580 nm (in chloroform).

EXAMPLE 3

138 g of 2,5,5-trimethyl-cyclopent-2-ene-1,4-dione are dissolved in 1000 ml of methanol. The solution is treated with 10 g of solid sodium borohydride while stirring at −20° C. After the reaction fades away, the mixture is introduced into a saturated aqueous sodium chloride solution and extracted with ethyl acetate. The extract is evaporated under reduced pressure. The residual crude 4-hydroxy-2,5,5-trimethyl-cyclopent-2-en-1-one boils at 85°–87° C./0.5 mmHg after rectification.

EXAMPLE 4

97 g of 4-hydroxy-2,5,5-trimethyl-cyclopent-2-en-1-one are dissolved in 600 ml of ether. After the addition of 90 ml of triethylamine, the solution is treated dropwise at 0° C. with 81 ml of trimethylchlorosilane and stirred at 0° C. for 4 hours. The mixture is then introduced into water and extracted with ether. The ether extract is washed with water, dried over sodium sulfate and evaporated under reduced pressure. The residual 2,5,5-trimethyl-4-[(trimethylsilyl)oxy]-cyclopent-2-en-1-one boils at 40°–43° C./0.02 mmHg.

EXAMPLE 5

12.1 g of trimethyl-[(trans-3-methyl-pent-2-en-4-yn-1-yl)oxy]-silane are dissolved in 150 ml of tetrahydrofuran. The solution is added dropwise to a Grignard solution prepared from 1.73 g of magnesium shavings and 7.78 g of ethyl bromide. The mixture is stirred for 1 hour and then, after the addition of a solution of 10.1 g of 2,5,5-trimethyl-4-[(trimethylsilyl)-oxy]-cyclopent-2-en-1-one in 50 ml of tetrahydrofuran, for a further 20 hours. The mixture is then introduced into a saturated aqueous ammonium chloride solution and extracted with ether. The extract is evaporated under reduced pressure. The residual 5-[2,5,5-trimethyl-1-hydroxy-4-[(trimethylsilyl)oxy]-cyclopent-2-en-1-yl]-3-methyl-1-[(trimethylsilyl)oxy]-pent-2-en-4-yne, a mixture of two isomers, is dissolved in 140 ml of methanol without purification and separation. After the addition of 28 ml of 5% by weight aqueous potassium hydroxide, the solution is stirred for 5 minutes, subsequently introduced into a saturated aqueous sodium chloride solution and extracted with ether. The ether extract is evaporated under reduced pressure. The residual 5-[1,4-dihydroxy-2,5,5-trimethyl-cyclopent-2-en-1-yl]-trans-3-methyl-pent-2-en-4-yn-1-ol is a mixture of two isomers.

EXAMPLE 6

90.4 g of 5-[1,4-dihydroxy-2,5,5-trimethyl-cyclopent-2-en-1-yl]-trans-3-methyl-pent-2-yn-1-ol are dissolved in 1400 ml of methylene chloride. The solution is treated with 380 ml of 98% formic acid, stirred for 45 minutes and subsequently introduced into water. The organic phase is separated and evaporated under reduced pressure. The residue is taken up in 780 ml of methanol, treated with 200 g of potassium carbonate in 500 ml of water, stirred for 1 hour, introduced into water and extracted with ethyl acetate. The 5-[3,4-dihydroxy-2,5,5-trimethyl-cyclopent-1-en-1-yl]-3-methyl-pent-2-en-4-yn-1-ol isolated from the extract melts at 121°–122° C.

EXAMPLE 7

2.35 g of 5-[3,4-dihydroxy-2,5,5-trimethyl-cyclopent-1-en-1-yl]-3-methyl-pent-2-en-4-yn-1-ol are dissolved in 200 ml of methylene chloride. After the addition of 90 g of activated manganese dioxide, the solution is stirred for 1 hour at room temperature. The mixture is then filtered. The filtrate is evaporated under reduced pressure. The residual 5-[3,4-dioxo-2,5,5-trimethyl-cyclopent-1-en-1-yl]-3-methyl-pent-2-en-4-yn-1-al melts at 141°–142° C. after purification by adsorption on silica gel.

5-[3-Oxo-4-hydroxy-2,5,5-trimethyl-cyclopent-1-en-1-yl]-3-methyl-pent-2-en-4-yn-1-al can be isolated as the byproduct.

EXAMPLE 8

4 g of 5-[3,4-dioxo-2,5,5-trimethyl-cyclopent-1-en-1-yl]-3-methyl-pent-2-en-4-yn-1-al are dissolved in 100 ml of ethyl acetate. The solution is shaken in a hydrogen atmosphere in the presence of 1 g of partially deactivated palladium catalyst (Lindlar catalyst) at room temperature and normal pressure until the calculated amount of hydrogen has been taken up. The catalyst is separated. The filtrate is evaporated under reduced pressure. The residual 5-[3,4-dioxo-2,5,5-trimethyl-cyclopent-1-en-1-yl]-3-methyl-penta-2,4-dien-1-al is further processed as follows without purification.

EXAMPLE 9

4.64 g of 5-[3,4-dioxo-2,5,5-trimethyl-cyclopent-1-en-1-yl]-3-methyl-penta-2,4-dien-1-al are dissolved in 150 ml of tetrahydrofuran. The solution is treated dropwise at −70° C. with 250 mg of sodium borohydride in 5 ml of water. After 20 minutes, the mixture is introduced into a saturated aqueous sodium chloride solution and extracted with ethyl acetate. The extract is evaporated under reduced pressure. The residual 5-[3,4-dioxo-2,5,5-trimethyl-cyclopent-1-en-1-yl]-3-methyl-penta-2,4-dien-1-ol is converted as follows in the desired phosphonium salt without further purification.

EXAMPLE 10

4.6 g of 5-[3,4-dioxo-2,5,5-trimethyl-cyclopent-1-en-1-yl]-3-methyl-penta-2,4-dien-1-ol are dissolved in 20 ml of methylene chloride. The solution is added dropwise at 0° C. to a suspension of 3.6 g of N-bromosuccinimide in 20 ml of methylene chloride and 2 ml of dimethylsulfide. The mixture is stirred at 0° C. for 2 hours, then introduced into water and extracted with ether/hexane (2:1 parts by volume). The crude 5-[3,4-dioxo-2,5,5-trimethyl-cyclopent-1-en-1-yl]-3-methyl-penta-2,4-diene-1-bromide remaining after evaporation of the extract is dissolved in 70 ml of ethyl acetate. The solution is treated with 5.3 g of triphenylphosphine. The 5-[3,4-dioxo-2,5,5-trimethyl-cyclopent-1-en-1-yl]-3-methyl-penta-2,4-diene-1-triphenylphosphonium bromide which separates in the course of 24 hours is dried in a high vacuum.

EXAMPLE 11

5.6 g of 3-[3-oxo-4-phenoxyacetyl-2,5,5-trimethyl-cyclopent-1-en-1-yl]-3-methyl-pent-2-en-4-yne-1-triphenylphosphonium bromide and 0.43 g of 2,7-dimethyl-octa-2,6-dien-4-yne-1,8-dial are dissolved in 100 ml of isopropanol. After the addition of 4.1 ml of 2-N sodium methylate, the solution is stirred at room temperature for 1 hour. The mixture is then introduced into water and extracted with methylene chloride. The 2,2′-dinor-7,7′,8,8′,15,15′-hexadehydroastaxanthin remaining after evaporation of the extract is purified by adsorption on silica gel. In the mass spectrum the compound shows the expected molecular weight of 562.

EXAMPLE 12

860 mg of 2,2′-dinor-7,7′,8,8′,15,15′-hexadehydroastaxanthin are dissolved in 200 ml of toluene. After the addition of 300 mg of partially deactivated palladium catalyst (Lindlar catalyst), the mixture is hydrogenated in a hydrogen atmosphere at room temperature and normal pressure until the calculated amount of hydrogen has been taken up. The catalyst is then separated. The actinioerythrol [2,2′-dinor-astaxanthin] remaining after evaporation of the filtrate melts at 207°–208° C. after recrystallization from methylene chloride/hexane.

EXAMPLE 13

270 mg of 2,2′-dinor-7,7′,8,8′,15,15′-hexadehydroastaxanthin are dissolved in 80 ml of toluene. After the addition of 0.7 g of solid sodium carbonate, air is blown through the solution until the greater portion of the starting has been converted into 2,2′-dinor-7,7′,8,8′,15,15′-hexadehydroastacene. The mixture is filtered. The crude product remaining after evaporation of the filtrate is purified by adsorption on silica gel. The mass spectrum shows a molecular weight of 558. The pure 2,2′-dinor-7,7′, 8,8′,15,15′-hexadehydroastacene can be converted into violerythrin [2,2′-dinor-astacene] in the same manner as described in Example 12 for the hydrogenation of 2,2′-dinor-7,7′,8,8′,15,15′-hexadehydroastaxanthin to actinioerythrol.

EXAMPLE 14

50 g of the 5-[3,4-dihydroxy-2,5,5-trimethyl-cyclopent-1-en-1-yl]-3-methyl-pent-2-en-4-yn-1-ol are dissolved in 300 ml of dioxan. After the addition of 120 g of 2,3-dichloro-5,6-dicyano-benzoquinone, the solution is stirred at 80° C. for 5 hours. The mixture is then cooled. The 2,3-dichloro-5,6-dicyano-benzohydroquinone which separates as the byproduct is filtered off. The 5-[3-oxo-4-hydroxy-2,5,5-trimethyl-cyclopent-1-en-1-yl]-3-methyl-pent-2-en-4-yn-1-al, an oil, remains after evaporation of the filtrate and is purified by adsorption on silica gel.

EXAMPLE 15

34 g of 5-[3-oxo-4-hydroxy-2,5,5-trimethyl-cyclopent-1-en-1-yl]-3-methyl-pent-2-en-4-yn-1-al are dissolved in 400 ml of ether. After the addition of 15 ml of pyridine, the solution is treated dropwise at −20° C. with 30 g of phenoxyacetic acid chloride. After 30 minutes, the mixture is introduced into water and extracted with ether. The 5-[3-oxo-4-phenoxy-acetyl-2,5,5-trimethyl-cyclopent-1-en-1-yl]-3-methyl-pent-2-en-4-yn-1al, an oil, which remains after evaporation of the ether is purified by adsorption on silica gel.

EXAMPLE 16

42 g of 5-[3-oxo-4-phenoxyacetyl-2,5,5-trimethyl-cyclopent-1-en-1-yl]-3-methyl-pent-2-en-4-yn-1-al are dissolved in 420 ml of ethanol. The solution is treated at −40° C. with 1.16 g of sodium borohydride and stirred for 10 minutes. The mixture is then introduced into water and extracted with ether. The 5-[3-oxo-4-phenoxyacetyl-2,5,5-trimethyl-cyclopent-1-en-1-yl]-3-methyl-pent-2-en-4-yn-1-ol is obtained as a viscous oil.

EXAMPLE 17

41 g of 5-[3-oxo-4-phenoxyacetyl-2,5,5-trimethyl-cyclopent-1-en-1-yl]-3-methyl-pent-2-en-4-yn-1-ol are dissolved in 300 ml of dimethylformamide. The solution is treated at 0° C. with 4.2 ml of phosphorus tribromide. After 1 hour, the mixture is introduced into water and extracted with ether. The bromide which remains after evaporation of the extract is taken up in 300 ml of ethyl acetate and treated with 30 g of triphenylphosphine. The 5-[3-oxo-4-phenoxyacetyl-3,5,5-trimethyl-cyclopent-1-en-1-yl]-3-methyl-pent-2-en-4-yne-1-triphenylphosphonium bromide which separates in the course of 24 hours is a sticky oil which solidifies in the form of a digestion with ethyl acetate and drying in a vacuum.

EXAMPLE 18

11 g of 5-[3-oxo-4-acetoxy-2,5,5-trimethyl-cyclopent-1-en-1-yl]-3-methyl-penta-2,4-diene-1-triphenylphosphonium bromide and 950 mg of 2,7-dimethyl-octa-2,6-dien-4-yne-1,8-dial are dissolved in 150 ml of isopropanol. After the addition of 9 ml of 2-N sodium methylate, the solution is stirred at room temperature for 3 hours. The mixture is then introduced into water and extracted with methylene chloride. The 15,15′-didehydroactinioerythrol diacetate which remains after evaporation of the extract shows a U.V. maximum at 487 nm (in chloroform).

EXAMPLE 19

1 g of 15,15′-didehydroactinioerythrol diacetate is dissolved in 200 ml of toluene. The solution is treated, with the complete exclusion of air, with an equivalent amount of 2-N sodium methylate until the control by thin-layer chromatography indicates the end of the reaction. The mixture is introduced into water. The organic phase is separated and evaporated. The residual 15,15′-didehydroactinioerythrol contaminated by 15,15′-didehydroviolerythrin can be purified by adsorption on silica gel.

EXAMPLE 20

420 mg of the resulting crude 15,15′-didehydroactinioerythrol are dissolved in 100 ml of toluene. After the addition of 1 g of solid sodium carbonate, air is blown through the solution until the greater portion of the starting material has been converted into 15,15′-didehydroviolerythrin. The mixture is filtered. The 5,15′-didehydroviolerythrin which remains after evaporation of the filtrate is purified by adsorption on silica gel. The mass spectrum shows a molecular weight of 562. U.V. maximum: 520 nm (in chloroform).

EXAMPLE 21

1.2 g of 15,15′-didehydroactinioerythrol are dissolved in 280 ml of toluene. After the addition of 0.8 g of partially deactivated palladium catalyst (Lindlar catalyst), the solution is hydrogenated in a hydrogen atmosphere at room temperature and normal pressure until the calculated amount of hydrogen has been taken up. The catalyst is then separated. The actinioerythrol which remains after evaporation of the filtrate melts at 207°–208° C. after recrystallization from methylene chloride/hexane.

EXAMPLE 22

In the same manner as in Example 21, 15,15′-didehydroactinioerythrol diacetate can be hydrogenated to actinioerythrol diacetate; U.V. maximum: 518 nm (in chloroform).

EXAMPLE 23

1 g of the 5-[3-oxo-4-hydroxy-2,5,5-trimethyl-cyclopent-1-en-1-yl]-3-methyl-pent-2-en-4-yn-1-al is dissolved in 250 ml of ethyl acetate. After the addition of 5 g of partially deactivated palladium catalyst (Lindlar catalyst), the solution is hydrogenated at room temperature and normal pressure with the addition of 0.24 ml of quinoline until the calculated amount of hydrogen has been taken up. The catalyst is separated. The 5-[3-oxo-4-hydroxy-2,5,5-trimethyl-cyclopent-1-en-1-yl]-3-methyl-penta-2,4-dien-1-al which remains after evaporation of the filtrate is processed as follows without further purification.

EXAMPLE 24

55 g of 5-[3-oxo-4-hydroxy-2,5,5-trimethyl-cyclopent-1-en-1-yl]-3-methyl-penta-2,4-dien-1-al are dissolved in 700 ml of ether. After the addition of 100 ml of pyridine, the solution is treated dropwise at −20° C. with 25 ml of acetyl chloride. After 30 minutes, the mixture is introduced into water and extracted with ether. The practically pure, oily 5-[3-oxo-4-acetoxy-2,5,5-trimethyl-cyclopent-1-en-1-yl]-3-methyl-penta-2,4-dien-1-al remains after evaporation of the extract.

EXAMPLE 25

10 g of 5-[3-oxo-4-acetoxy-2,5,5-trimethyl-cyclopent-1-en-1-yl]-3-methyl-penta-2,4-dien-1-al are dissolved in 200 ml of tetrahydrofuran and 10 ml of water. 1.5 g of sodium borohydride are introduced portionwise into the solution at −45° C. After 30 minutes, the mixture is introduced into a saturated aqueous sodium chloride solution and extracted with ether. The practically pure, oily 5-[3-oxo-4-acetoxy-2,5,5-trimethylcyclopent-1-en-1-yl]-3-methyl-pent-2,4-dien-1-ol [I. R. spectrum: 3550 cm$^{-1}$] remains after evaporation of the extract.

EXAMPLE 26

7.35 g of 5-[3-oxo-4-acetoxy-2,5,5-trimethyl-cyclopent-1-en-1-yl]-3-methyl-penta-2,4-dien-1-ol are dissolved in 20 ml of methylene chloride. The solution is introduced into a suspension of 9 g of N-bromosuccinimide in 15 ml of methylene chloride and 5 ml of dimethylsulfide. The mixture is stirred at room temperature for 1 hour, then introduced into water and extracted with ether. The crude 5-[3-oxo-4-acetoxy-2,5,5-trimethylcyclopent-1-en-1-yl]-3-methyl-penta-2,4-diene-1-bromide which remains after evaporation of the extract is dissolved in 100 ml of ethyl acetate. The solution is treated with 7 g of triphenylphosphine. The 5-[3-oxo-4-acetoxy-2,5,5-trimethyl-cyclopent-1-en-1-yl]-3-methyl-penta-2,4-diene-1-triphenylphosphonium bromide which separates in crystalline form in the course of 24 hours melts at 212°–215° C.

EXAMPLE 27

7.4 g of 5-[3,4-dioxo-2,5,5-trimethyl-cyclopent-1-en-1-yl]-3-methyl-pent-2-en-4-yne-1-triphenylphosphonium bromide are stirred at room temperature for 3 hours together with 0.9 g of 2,7-dimethyl-octa-2,6-dien-4-yne-1,8-dial in 100 ml of butylene oxide. The mixture is subsequently evaporated. The residual 2,2'-dinor-7,7',8,8',15,15'-hexadehydroastacene [7,7',8,8',15,15'-hexadehydroviolerythrin] can be converted by partial hydrogenation into violerythrin as described in Example 12.

EXAMPLE 28

5.7 g of the 5-[3,4-dioxo-2,5,5-trimethyl-cyclopent-1-en-1-yl]-3-methyl-pent-2-en-4-yn-1-al obtained according to Example 1 are dissolved in 100 ml of tetrahydrofuran. The solution is treated at −70° C. while stirring with 260 mg of sodium borohydride in 5 ml of water. After 30 minutes, the mixture is introduced into a saturated aqueous sodium chloride solution and extracted with ethyl acetate. The 5-[3,4-dioxo-2,5,5-trimethylcyclopent-1-en-1-yl]-3-methyl-pent-2-en-4-yn-1-ol remains after evaporation of the extract.

EXAMPLE 29

2.3 g of 5-[3,4-dioxo-2,5,5-trimethyl-cyclopent-1-en-1-yl]-3-methyl-pent-2-en-4-yn-1-ol are dissolved in 20 ml of methylene chloride. The solution is added dropwise at 0° C. to a suspension of 2 g of N-bromosuccinimide in 20 ml of methylene chloride and 3 ml of dimethylsulfide. After 2 hours, the mixture is introduced into water and extracted with ether/hexane (2:1 parts by volume). The crude 5-[3,4-dioxo-2,5,5-trimethyl-cyclopent-1-en-1-yl]-3-methyl-pent-2-en-4-yne-1-bromide which remains after evaporation of the extract is dissolved in 100 ml of ethyl acetate. The solution is treated with 2.6 g of triphenylphosphine. The sticky, oily 5-[3,4-dioxo-2,5,5-trimethyl-cyclopent-1-en-1-yl]-3-methyl-pent-2-en-4-yne-1-triphenylphosphonium bromide is dried in a high vacuum after separation of the supernatant solvent. Infrared spectrum: 1755 cm$^1$; 1696 cm$^1$.

EXAMPLE 30

Production of a coloring preparation suitable for the coloring of foodstuffs:

1.0 g of 15,15'-didehydroviolerythrin, 0.1 g. of d,1-α-tocopherol, 0.4 g of arachis oil and 1.0 g of ascorbyl palmitate are dissolved in 50 ml of hot chloroform. The solution is homogenized with 4.1 g of gelatin, 1.7 g of sugar, 1.7 g of yellow dextrin and 0.2 g of sodium carbonate-dissolved in 50 ml of water. The homogenate is poured on to a metal sheet, dried chloroform-free in a vacuum and pulverized.

1–50 g of the previously obtained coloring preparation are required for the coloring of 100 kg of candy mass. The coloring preparation, dissolved in 10–500 ml of warm water, is added to the candy mass together with the aromas (e.g. redcurrant or raspberry aroma) and the resulting mixture is homogeneously mixed.

I claim:

1. A compound of the formula

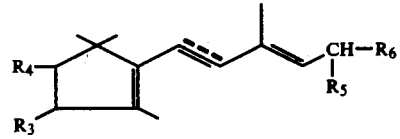

wherein $R_5$ is hydroxy, $R_6$ is hydrogen, or $R_5$ and $R_6$ taken together forms oxo; $R_4$ is hydroxy, oxo or acyloxy; $R_3$ is oxo or hydroxy, with the proviso that when $R_5$ is hydroxy and $R_4$ is oxo or acyloxy, $R_3$ is oxo and the dotted bond can be optionally hydrogenated and with the further proviso that when $R_5$ and $R_6$ are oxo, $R_3$ is oxo.

2. The compound of claim 1 wherein said compound is 5-[3,4-dioxo-2,5,5-trimethyl-cyclopent-1-en-1-yl]-3-methyl-pent-2-en-4-yn-1-al.

3. The compound of claim 1 wherein said compound is 5-[3-oxo-4-acetoxy-2,5,5-trimethyl-cyclopent-1-en-1-yl]-3-methyl-pent-2,4-dien-1-ol.

4. The compound of claim 1 wherein said compound is 5-[3-oxo-4-acetoxy-2,5,5-trimethyl-cyclopent-1-en-1-yl]-3-methyl-penta-2,4-dien-1-al.

* * * * *